United States Patent
Friedrichs et al.

(10) Patent No.: US 10,610,285 B2
(45) Date of Patent: Apr. 7, 2020

(54) ELECTROSURGICAL GENERATORS

(71) Applicant: COVIDIEN LP, Mansfield, MA (US)

(72) Inventors: Daniel Friedrichs, Aurora, CO (US); James A. Gilbert, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 459 days.

(21) Appl. No.: 14/174,607

(22) Filed: Feb. 6, 2014

(65) Prior Publication Data
US 2015/0025521 A1    Jan. 22, 2015

Related U.S. Application Data (60) Provisional application No. 61/856,480, filed on Jul. 19, 2013.

(51) Int. Cl.
*A61B 18/12* (2006.01)
*H02M 7/5387* (2007.01)
(Continued)

(52) U.S. Cl.
CPC ..... *A61B 18/1206* (2013.01); *H02M 7/53871* (2013.01); *A61B 2018/0063* (2013.01);
(Continued)

(58) Field of Classification Search
CPC ...... A61B 18/1206; A61B 2018/00648; A61B 2018/00726; A61B 2018/0072;
(Continued)

(56) References Cited

U.S. PATENT DOCUMENTS 3,252,052 A    5/1966    Nash
3,514,689 A    5/1970    Giannamore
(Continued)

FOREIGN PATENT DOCUMENTS

CN    102149345 A    8/2011
DE       179607 C    3/1905
(Continued)

OTHER PUBLICATIONS

Wald et al., "Accidental Burns", JAMA, Aug. 16, 1971, vol. 217, No. 7, pp. 916-921.
(Continued)

*Primary Examiner* — Ronald Hupczey, Jr.
(74) *Attorney, Agent, or Firm* — Carter, DeLuca & Farrell LLP (57) ABSTRACT

An electrosurgical generator is provided. The electrosurgical generator includes at least one converter configured to output a DC waveform and a nonlinear carrier control current. At least one boost inverter is coupled to the at least one converter and is configured to convert the DC waveform to generate at least one electrosurgical waveform. At least one inductor is connected in series with the at least one converter and at least one boost inverter and is configured to output an inductor current. A controller is coupled to the at least one converter and the at least one boost inverter and is configured to maintain the inductor current at a predetermined value by controlling a pulse duration of a duty cycle of the at least one converter based on a comparison of inductor current and the nonlinear control current.

16 Claims, 7 Drawing Sheets

(51) Int. Cl.
    *A61B 18/00*    (2006.01)
    *H02M 1/00*    (2006.01)
(52) U.S. Cl.
    CPC ............ *A61B 2018/00577* (2013.01); *A61B 2018/00589* (2013.01); *A61B 2018/00601* (2013.01); *A61B 2018/00625* (2013.01); *A61B 2018/00642* (2013.01); *A61B 2018/00678* (2013.01); *A61B 2018/00726* (2013.01); *A61B 2018/00779* (2013.01); *A61B 2018/00827* (2013.01); *A61B 2018/00892* (2013.01); *A61B 2018/128* (2013.01); *H02M 2001/007* (2013.01)
(58) Field of Classification Search
    CPC ........... A61B 2018/00827; A61B 2018/00773; A61B 2018/1226
    See application file for complete search history.

(56) References Cited

U.S. PATENT DOCUMENTS

| | | | |
|---|---|---|---|
| 3,551,786 A | 12/1970 | Van Gulik | |
| 3,641,422 A | 2/1972 | Farnsworth et al. | |
| 3,801,800 A | 4/1974 | Newton | |
| 3,885,569 A | 5/1975 | Judson | |
| 3,897,787 A | 8/1975 | Ikuno et al. | |
| 3,978,393 A | 8/1976 | Wisner et al. | |
| 4,102,341 A | 7/1978 | Ikuno et al. | |
| 4,287,557 A | 9/1981 | Brehse | |
| 4,378,801 A | 4/1983 | Oosten | |
| 4,416,276 A | 11/1983 | Newton et al. | |
| 4,416,277 A | 11/1983 | Newton et al. | |
| 4,436,091 A | 3/1984 | Banko | |
| 4,438,766 A | 3/1984 | Bowers | |
| 4,559,943 A | 12/1985 | Bowers | |
| 4,569,345 A | 2/1986 | Manes | |
| 4,572,190 A | 2/1986 | Azam et al. | |
| 4,590,934 A | 5/1986 | Malis et al. | |
| 4,630,218 A | 12/1986 | Hurley | |
| 4,644,955 A | 2/1987 | Mioduski | |
| 4,658,815 A | 4/1987 | Farin et al. | |
| 4,658,820 A | 4/1987 | Klicek | |
| 4,691,703 A | 9/1987 | Auth et al. | |
| 4,739,759 A | 4/1988 | Rexroth et al. | |
| 4,754,757 A | 7/1988 | Feucht | |
| 4,767,999 A | 8/1988 | VerPlanck | |
| 4,860,745 A | 8/1989 | Farin et al. | |
| 4,887,199 A | 12/1989 | Whittle | |
| 4,959,606 A | 9/1990 | Forge | |
| 5,304,917 A | 4/1994 | Somerville | |
| 5,334,183 A | 8/1994 | Wuchinich | |
| 5,370,672 A | 12/1994 | Fowler et al. | |
| 5,438,302 A | 8/1995 | Goble | |
| 5,472,443 A | 12/1995 | Cordis et al. | |
| 5,500,616 A | 3/1996 | Ochi | |
| 5,531,774 A | 7/1996 | Schulman et al. | |
| 5,540,684 A | 7/1996 | Hassler, Jr. | |
| 5,558,671 A | 9/1996 | Yates | |
| 5,559,688 A | 9/1996 | Pringle | |
| 5,596,466 A | 1/1997 | Ochi | |
| 5,658,322 A | 8/1997 | Fleming | |
| 5,674,217 A | 10/1997 | Wahlstrom et al. | |
| 5,694,304 A | 12/1997 | Telefus et al. | |
| 5,712,772 A | 1/1998 | Telefus et al. | |
| 5,817,093 A | 10/1998 | Williamson, IV et al. | |
| 5,836,943 A | 11/1998 | Miller, III | |
| 5,871,481 A | 2/1999 | Kannenberg et al. | |
| 6,017,354 A | 1/2000 | Culp et al. | |
| 6,044,283 A | 3/2000 | Fein et al. | |
| 6,063,075 A | 5/2000 | Mihori | |
| 6,090,123 A | 7/2000 | Culp et al. | |
| 6,142,992 A | 11/2000 | Cheng et al. | |
| 6,162,217 A | 12/2000 | Kannenberg et al. | |
| 6,235,020 B1 | 5/2001 | Cheng et al. | |
| 6,296,636 B1 | 10/2001 | Cheng et al. | |
| 6,329,778 B1 | 12/2001 | Culp et al. | |
| 6,629,974 B2 | 10/2003 | Penny et al. | |
| 6,723,091 B2 | 4/2004 | Goble et al. | |
| 6,740,079 B1 | 5/2004 | Eggers et al. | |
| 6,923,804 B2 | 8/2005 | Eggers et al. | |
| 7,004,174 B2 | 2/2006 | Eggers et al. | |
| 7,244,255 B2 | 7/2007 | Daners et al. | |
| 7,364,972 B2 | 4/2008 | Ono et al. | |
| D574,323 S | 8/2008 | Waaler | |
| 7,722,603 B2 | 5/2010 | McPherson | |
| 7,863,841 B2 | 1/2011 | Menegoli et al. | |
| 2004/0082946 A1 | 4/2004 | Malis et al. | |
| 2007/0040516 A1* | 2/2007 | Chen ................ H05B 39/045 315/291 |
| 2011/0087213 A1 | 4/2011 | Messerly et al. | |
| 2011/0319881 A1 | 12/2011 | Johnston | |
| 2013/0035679 A1 | 2/2013 | Orszulak | |
| 2013/0053840 A1 | 2/2013 | Krapohl et al. | |
| 2013/0066311 A1 | 3/2013 | Smith et al. | |
| 2013/0067725 A1 | 3/2013 | Behnke, II et al. | |
| 2013/0072920 A1 | 3/2013 | Behnke, II et al. | |
| 2013/0072921 A1 | 3/2013 | Behnke, II et al. | |
| 2013/0072922 A1 | 3/2013 | Behnke, II et al. | |
| 2013/0072923 A1 | 3/2013 | Behnke, II et al. | |
| 2013/0079673 A1 | 3/2013 | Stein et al. | |
| 2013/0190751 A1 | 7/2013 | Brannan | |
| 2013/0193952 A1 | 8/2013 | Krapohl | |
| 2013/0197510 A1 | 8/2013 | Heckel | |
| 2013/0197874 A1 | 8/2013 | Heckel | |
| 2013/0249721 A1 | 9/2013 | Smith | |
| 2013/0253501 A1 | 9/2013 | Joseph | |
| 2013/0261616 A1 | 10/2013 | Prakash et al. | |
| 2013/0267944 A1 | 10/2013 | Krapohl | |
| 2013/0274729 A1 | 10/2013 | Orszulak | |
| 2013/0304049 A1 | 11/2013 | Behnke, II et al. | |
| 2013/0345696 A1 | 12/2013 | Behnke, II et al. | |
| 2014/0002056 A1 | 1/2014 | Moul et al. | |
| 2014/0015535 A1 | 1/2014 | Lopez | |

FOREIGN PATENT DOCUMENTS

| | | |
|---|---|---|
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |

(56) References Cited

FOREIGN PATENT DOCUMENTS

| EP | 694291 A1 | 1/1996 | |
| EP | 0 836 868 A2 | 4/1998 | |
| EP | 880220 A2 | 11/1998 | |
| EP | 0 882 955 A1 | 12/1998 | |
| EP | 1051948 A2 | 11/2000 | |
| EP | 1151725 A1 | 11/2001 | |
| EP | 1366724 A1 | 12/2003 | |
| EP | 1500378 A1 | 1/2005 | |
| EP | 1776929 A1 | 4/2007 | |
| EP | 2469699 A2 | 6/2012 | |
| EP | 2469699 A2 * | 6/2012 | ......... A61B 18/1206 |
| FR | 1 275 415 A | 11/1961 | |
| FR | 1 347 865 A | 1/1964 | |
| FR | 2 313 708 A1 | 12/1976 | |
| FR | 2364461 A1 | 4/1978 | |
| FR | 2 502 935 A1 | 10/1982 | |
| FR | 2 517 953 A1 | 6/1983 | |
| FR | 2 573 301 A1 | 5/1986 | |
| GB | 702510 A | 1/1954 | |
| GB | 1290304 A | 9/1972 | |
| GB | 2434872 A | 8/2007 | |
| JP | 63 005876 A | 1/1988 | |
| JP | 2002-065690 A | 3/2002 | |
| JP | 2005-185657 A | 7/2005 | |
| JP | 2012135203 A | 7/2012 | |
| SU | 166452 | 11/1964 | |
| SU | 727201 A2 | 4/1980 | |
| WO | 02/11634 A1 | 2/2002 | |
| WO | 02/45589 A2 | 6/2002 | |
| WO | 03/090635 A1 | 11/2003 | |
| WO | 06/050888 A1 | 5/2006 | |
| WO | 08/053532 A1 | 5/2008 | |
| WO | 2010025807 A1 | 3/2010 | |

OTHER PUBLICATIONS

Vallfors et al., "Automatically Controlled Bipolar Electrosoagulation—'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690, filed Apr. 3, 2003, Michael S. Klicek.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/943,518, filed Jul. 16, 2013, Orszulak et al.
U.S. Appl. No. 13/971,553, filed Aug. 20, 2013, Behnke.
U.S. Appl. No. 13/971,596, filed Aug. 20, 2013, Collins.
U.S. Appl. No. 14/048,946, filed Oct. 3, 2013, Wham.
U.S. Appl. No. 14/058,929, filed Oct. 21, 2013, Gilbert.
U.S. Appl. No. 14/058,957, filed Oct. 21, 2013, Gilbert.
U.S. Appl. No. 14/069,534, filed Nov. 1, 2013, Digmann.
U.S. Appl. No. 14/072,312, filed Nov. 5, 2013, Wham.
U.S. Appl. No. 14/072,342, filed Nov. 5, 2013, Wham.
U.S. Appl. No. 14/072,386, filed Nov. 5, 2013, Wham.
U.S. Appl. No. 14/096,341, filed Dec. 4, 2013, Johnson.
U.S. Appl. No. 14/098,859, filed Dec. 6, 2013, Johnson.
U.S. Appl. No. 14/100,113, filed Dec. 9, 2013, Gilbert.
U.S. Appl. No. 14/144,850, filed Dec. 31, 2013, Johnston.
U.S. Appl. No. 14/147,294, filed Jan. 3, 2014, Gilbert.
U.S. Appl. No. 14/147,312, filed Jan. 3, 2014, Gilbert.
Zhang et al., Deadbeat control of PWM inverter with repetitive disturbance prediction, Applied Power Elect Conf & Expo, APEC '99, 14th Annual, Dallas, TX, IEEE, vol. 2, pp. 1026-1031 (Mar. 1999).
Extended European Search Report for EP 14 17 7793 dated Nov. 20, 2014.
European Office Action for EP 14177793.8 dated Mar. 23, 2016.
Office Action issued by the Chinese Patent Office for corresponding application No. 201410342341.7, dated Sep. 1, 2017.
Japanese Office Action issued in related application No. 2014-142012, dated May 30, 2018.

* cited by examiner

ELECTROSURGICAL GENERATORS

CROSS-REFERENCE TO RELATED APPLICATIONS

The present application claims the benefit of and priority to U.S. Provisional Patent Application No. 61/856,480 filed by Friedrichs et al. on Jul. 19, 2013, the entire contents of which is hereby incorporated by reference.

BACKGROUND

Technical Field

The present disclosure relates to electrosurgical generators. More particularly, the present disclosure relates to electrosurgical generators that utilize current-programmed control with a nonlinear control current to produce a constant power source.

Background of Related Art

Electrosurgery involves application of high radio frequency electrical current to a surgical site to cut, ablate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes positioned on the instrument, e.g. forceps or the like. A forceps is a pliers-like instrument which relies on mechanical action between its jaws to grasp, clamp and constrict vessels or tissue. Electrosurgical forceps (open or endoscopic) utilize mechanical clamping action and electrical energy to effect hemostasis on the clamped tissue. The forceps include electrosurgical conductive surfaces which apply the electrosurgical energy to the clamped tissue. By controlling the intensity, frequency and duration of the electrosurgical energy applied through the conductive plates to the tissue, the surgeon can coagulate, cauterize and/or seal tissue. However, the above example is for illustrative purposes only and there are many other known bipolar electrosurgical instruments which are within the scope of the present disclosure.

Electrosurgical procedures outlined above may utilize various tissue and energy parameters in a feedback-based control system. There is continual need to improve delivery of energy to the tissue.

SUMMARY

As can be appreciated, electrosurgical generators that utilize current-programmed control with a nonlinear control current to produce a constant power source may prove useful in the surgical arena.

An aspect of the present disclosure provides an electrosurgical generator, which includes one or more converters configured to output a DC waveform and a nonlinear carrier control current. One or more boost inverters are coupled to the converter and are configured to convert the DC waveform to generate at least one electrosurgical waveform. One or more inductors are connected in series with the converter and the boost inverter. The inductor is configured to output an inductor current. One or more controllers are coupled to converter and the boost inverter and is configured to maintain the inductor current at a predetermined value by controlling a pulse duration of a duty cycle of the at least one converter based on a comparison of inductor current and the nonlinear control current.

The converter may be a DC-DC converter including but not limited to a DC-DC buck converter, a DC-DC Ćuk converter, a DC-DC buck-squared converter and a DC-DC inverse-SEPIC converter. Moreover, the boost inverter may be a DC-AC boost inverter. The converter and/or boost inverter may include a plurality of switching elements arranged in an H-bridge topology.

The controller is configured to adjust the duty cycle of the converter and a duty cycle of the boost inverter to operate the at least one electrosurgical waveform in at least one of constant current, constant voltage, or constant power modes. The converter may include one or more first switching elements operated at the duty cycle of the converter and the boost inverter may include one or more second switching elements operated at the second duty cycle of the boost inverter. The controller may be configured to control the converter in a current-program mode and to maintain the duty cycle of the boost inverter at about 100% to operate the at least one electrosurgical waveform in a constant current mode. Alternatively, the controller may be configured to control the converter in a non-linear carrier control mode and to maintain the duty cycle of the boost inverter at about 100% to operate the at least one electrosurgical waveform in a constant power mode. In the non-linear carrier control mode, the controller calculates a set point current based on a ratio of elapsed time and period length of each cycle of the DC waveform.

The controller may be configured to control the boost inverter in a current-program mode and to maintain the duty cycle of the converter at about 100% to operate the at least one electrosurgical waveform in a constant power mode. The controller may be configured to maintain the duty cycle of the converter at about 100% and the duty cycle of the boost inverter at less than 100% to operate the at least one electrosurgical waveform in a constant voltage mode. The controller may be configured to adjust the duty cycle of the at least one converter to control power of the at least one electrosurgical waveform.

The controller may be configured to switch operation of the at least one electrosurgical waveform between constant current, constant voltage and constant power modes based on the duty cycle of the at least one converter. Alternatively, the controller may be configured to switch operation of the at least one electrosurgical waveform between constant current, constant voltage, or constant power modes by monitoring a voltage of primary windings of a transformer of the electrosurgical generator and the inductor current.

An aspect of the instant disclosure provides a method for controlling an electrosurgical generator. Initially, a DC waveform and a nonlinear carrier control current from at least one converter may be output. Thereafter, a boost inverter may be utilized to convert the DC waveform to generate at least one electrosurgical waveform. Subsequently, an inductor current may be output from one or more inductors connected in series with the converter and boost inverter. And, the inductor current is maintained at a predetermined value by controlling pulse duration of a duty cycle of the converter based on a comparison of the inductor current and the nonlinear control current.

A DC-DC buck converter, DC-DC Ćuk converter, DC-DC buck-squared converter and DC-DC inverse-SEPIC converter may be utilized for the converter. Additionally, a DC-AC boost inverter may be utilized for the converter. The converter and boost inverter may be provided with a plurality of switching elements arranged in an H-bridge topology.

The duty cycle of the converter and a duty cycle of the boost inverter may be adjusted to operate the at least one electrosurgical waveform in at least one of constant current, constant voltage, or constant power modes.

The converter may be provided with one or more first switching elements operated at the duty cycle of the converter. And, the boost inverter may be provided with one or more second switching elements operated at the second duty cycle of the at least one boost inverter.

The converter may be controlled in a current-program mode and the duty cycle of the boost inverter may be maintained at about 100% to operate the at least one electrosurgical waveform in a constant current mode.

The converter may be controlled in a non-linear carrier control mode and the duty cycle of the boost inverter may be maintained at about 100% to operate the at least one electrosurgical waveform in a constant power mode. In the non-linear carrier control mode, a set point current is calculated based on a ratio of elapsed time and period length of each cycle of the DC waveform.

The converter may be controlled in a current-program mode and the duty cycle of the converter may be maintained at about 100% to operate the at least one electrosurgical waveform in a constant power mode. The duty cycle of the converter may be maintained at about 100% and the duty cycle of the boost inverter may be maintained at less than 100% to operate the at least one electrosurgical waveform in a constant voltage mode.

The duty cycle of the at least one converter may be adjusted to control power of the at least one electrosurgical waveform. Operation of the at least one electrosurgical waveform may be switched between constant current, constant voltage, and constant power modes based on the duty cycle of the at least one converter. Alternatively, operation of the at least one electrosurgical waveform may be switched between constant current, constant voltage, and constant power modes by monitoring a voltage of a primary winding of a transformer of the electrosurgical generator and the inductor current.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

A generator according to the present disclosure can perform monopolar and/or bipolar electrosurgical procedures, including, for example, cutting, coagulation, ablation, and vessel sealing procedures. The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cut, blend, coagulate, division with hemostasis, fulgurate, spray, etc.) and procedures (e.g., monopolar, bipolar, vessel sealing). In embodiments, the generator may be embedded, integrated or otherwise coupled to the electrosurgical instruments providing for an all-in-one electrosurgical apparatus.

Figure 1:
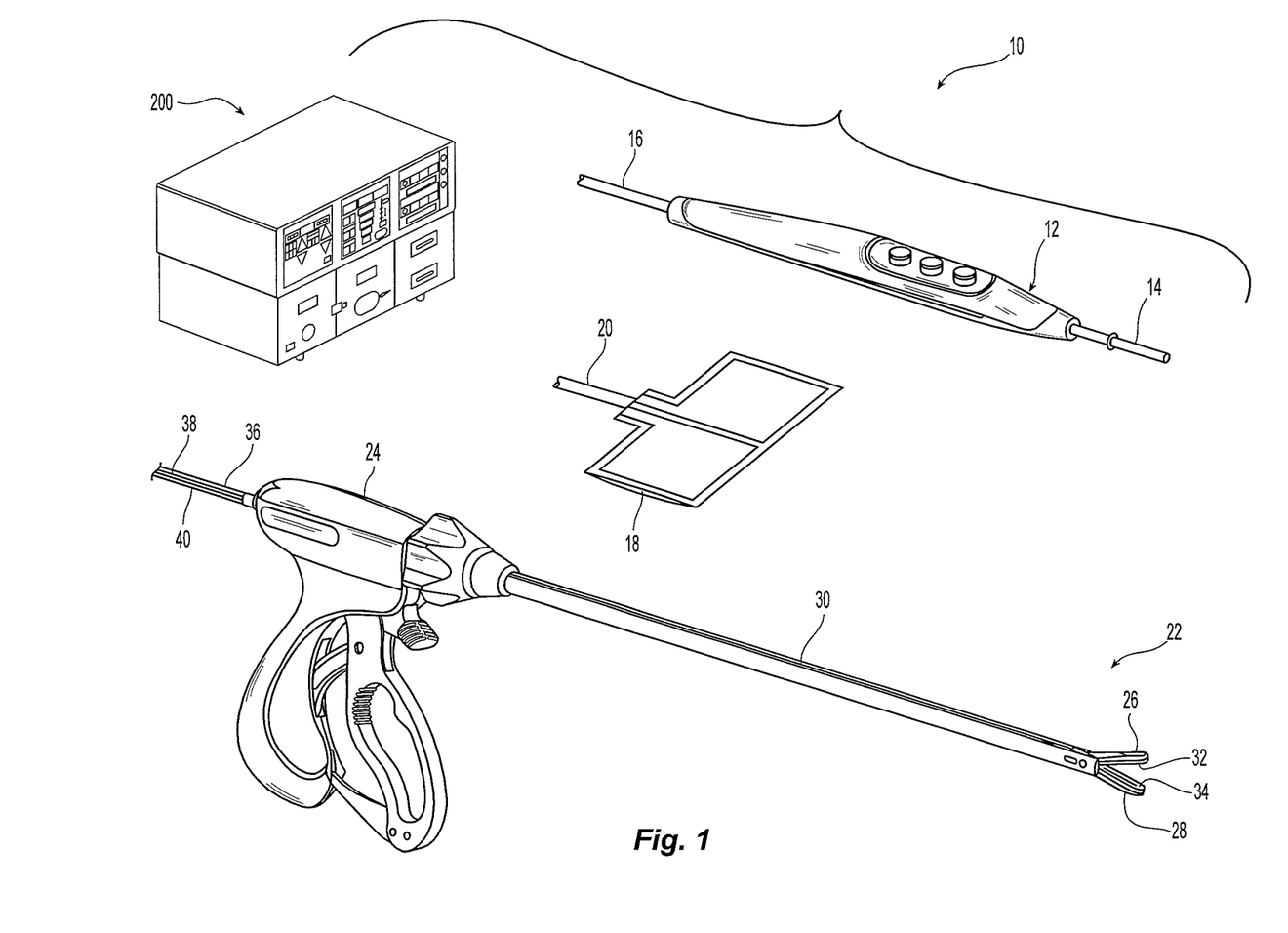
FIG. 1 is a perspective view of the components of one illustrative embodiment of an electrosurgical system according to the present disclosure.

FIG. 1 is a schematic illustration of a bipolar and monopolar electrosurgical system 10 according to the present disclosure. The system 10 may include one or more monopolar electrosurgical instruments 12 having one or more active electrodes 14 (e.g., electrosurgical cutting probe, ablation electrode(s), etc.) for treating tissue of a patient. Electrosurgical alternating current is supplied to the instrument 12 by a generator 200 via a supply line 16 that is connected to an active terminal 230 (FIG. 3) of the generator 200, allowing the instrument 12 to cut, coagulate, ablate and/or otherwise electrosurgically treat tissue. The alternating current is returned to the generator 200 through a return electrode pad 18 via a return line 20 at a return terminal 232 (FIG. 3) of the generator 200. For monopolar operation, the system 10 may include a plurality of return electrode pads 18 that, in use, are disposed on a patient to minimize the chances of tissue damage by maximizing the overall contact area with the patient. In addition, the generator 200 and the return electrode pads 18 may be configured for monitoring tissue-to-patient contact to ensure that sufficient contact exists therebetween.

Figure 3:
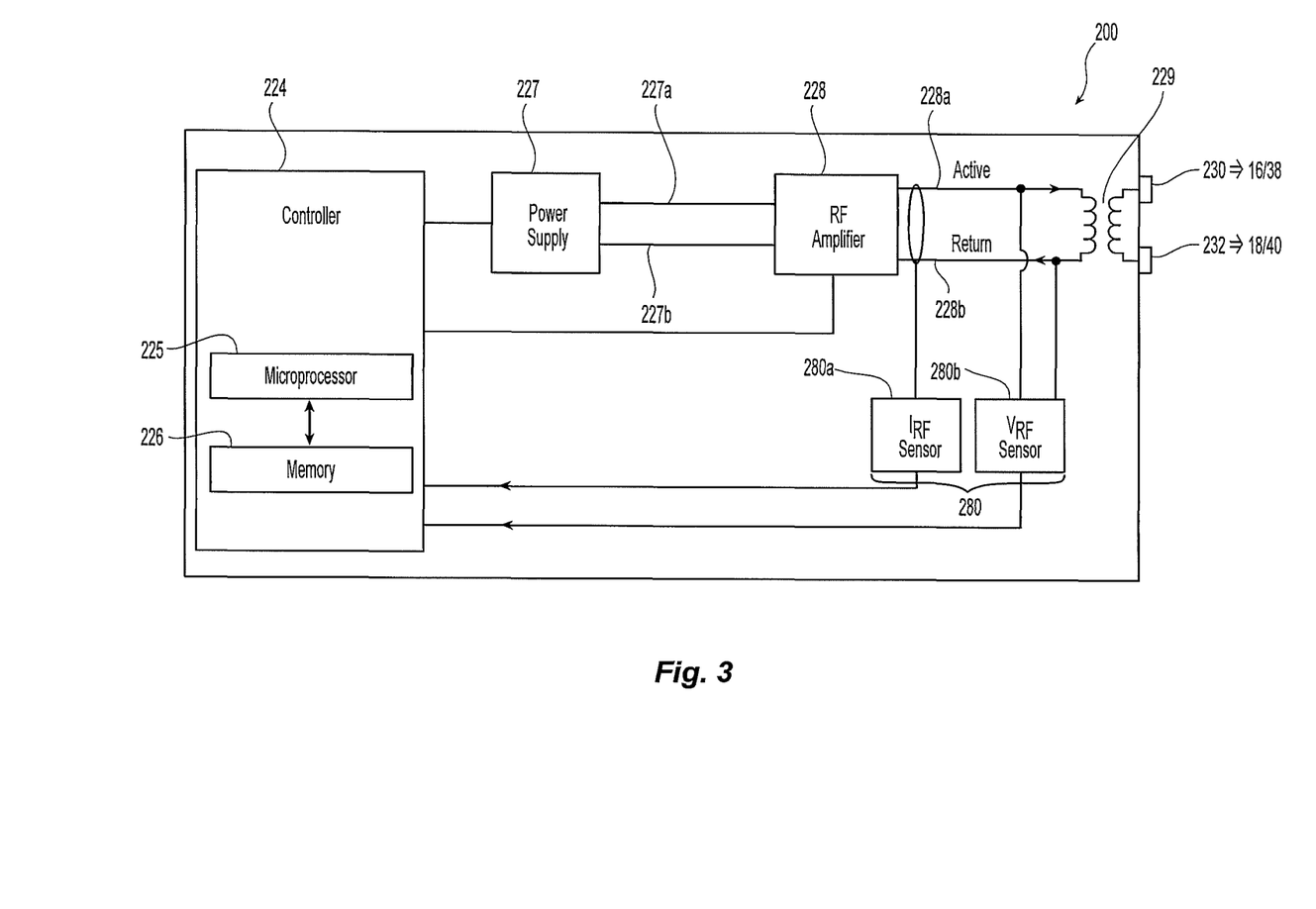
FIG. 3 is a schematic, block diagram of the embodiment of an electrosurgical generator of FIG. 2 according to the present disclosure.

The system 10 may also include one or more bipolar electrosurgical instruments, for example, a bipolar electrosurgical forceps 22 having one or more electrodes for treating tissue of a patient. The electrosurgical forceps 22 includes a housing 24 and opposing jaw members 26 and 28 disposed at a distal end of a shaft 30. The jaw members 26 and 28 have one or more active electrodes 32 and a return electrode 34 disposed therein, respectively. The active electrode 32 and the return electrode 34 are connected to the generator 200 through a cable 36 that includes supply and return lines 38, 40 coupled to the active and return terminals 230, 232, respectively (FIG. 3). The electrosurgical forceps 22 is coupled to the generator 200 at a connector having connections to the active and return terminals 230 and 232

(e.g., pins) via a plug disposed at the end of the cable 36, wherein the plug includes contacts from the supply and return lines 38, 40 as described in more detail below.

Figure 2:
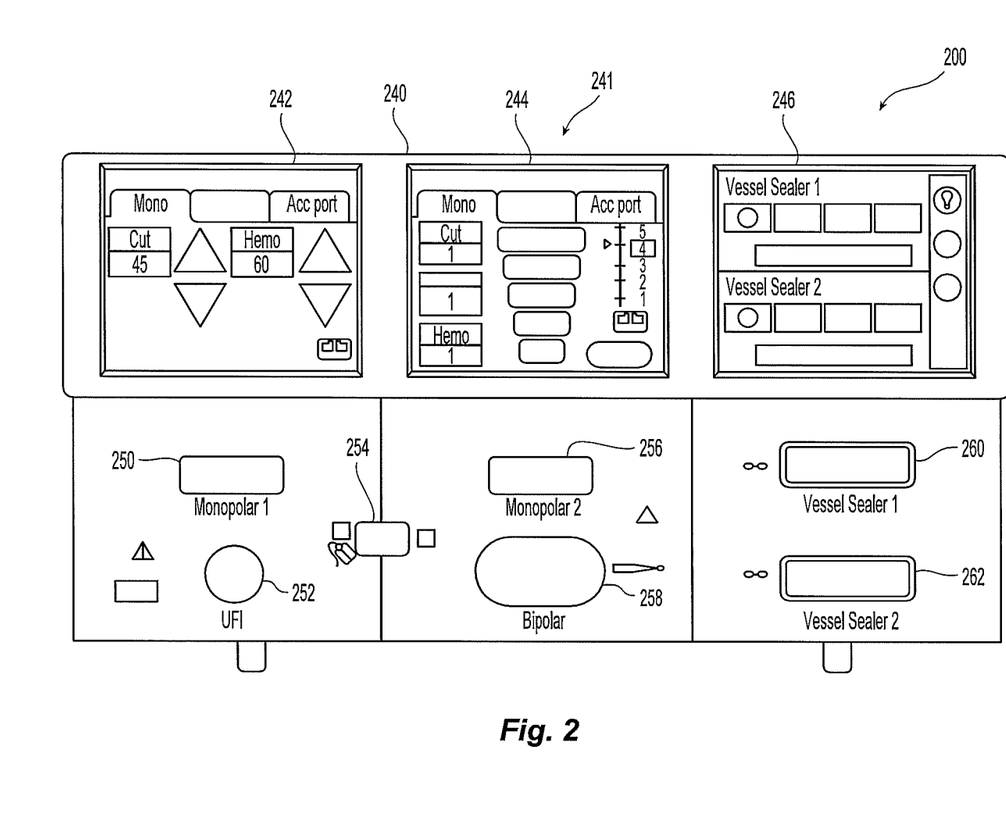
FIG. 2 is a front view of one embodiment of an electrosurgical generator according to the present disclosure.

With reference to FIG. 2, a front face 240 of the generator 200 is shown. The generator 200 may be any suitable type (e.g., electrosurgical, microwave, etc.) and may include a plurality of connectors 250-262 to accommodate various types of electrosurgical instruments (e.g., electrosurgical forceps 22, etc.).

The generator 200 includes a user interface 241 having one or more display screens or information panels 242, 244, 246 for providing the user with a variety of output information (e.g., intensity settings, treatment complete indicators, etc.). Each of the screens 242, 244, 246 is associated with corresponding connectors 250-262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., electrosurgical forceps 22, etc.). The user then adjusts inputs by simply touching corresponding menu options.

Screen 242 controls monopolar output and the devices connected to the connectors 250 and 252. Connector 250 is configured to couple to a monopolar electrosurgical instrument (e.g., electrosurgical instrument 12) and connector 252 is configured to couple to a foot switch (not shown). The foot switch provides for additional inputs (e.g., replicating inputs of the generator 200). Screen 244 controls monopolar and bipolar output and the devices connected to the connectors 256 and 258. Connector 256 is configured to couple to other monopolar instruments. Connector 258 is configured to couple to other bipolar instruments (not shown).

Screen 246 controls bipolar sealing procedures performed by the forceps 10 that may be plugged into the connectors 260 and 262. The generator 200 outputs energy through the connectors 260 and 262 suitable for sealing tissue grasped by the forceps 10. In particular, screen 246 outputs a user interface that allows the user to input a user-defined intensity setting. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to the controller 224 where the setting may be saved in memory 226. In embodiments, the intensity setting may be a number scale, such as for example, from one to ten or one to five. In embodiments, the intensity setting may be associated with an output curve of the generator 200. The intensity settings may be specific for each forceps 22 being utilized, such that various instruments provide the user with a specific intensity scale corresponding to the forceps 22.

FIG. 3 shows a schematic block diagram of the generator 200 configured to output electrosurgical energy. The generator 200 includes a controller 224, a power supply 227, and a radio-frequency (RF) amplifier 228. The power supply 227 may be a high voltage, DC power supply connected to an AC source (e.g., line voltage) and provides high voltage, DC power to the RF amplifier 228 via leads 227a and 227b, which then converts high voltage, DC power into treatment energy (e.g., electrosurgical or microwave) and delivers the energy to the active terminal 230. The energy is returned thereto via the return terminal 232. The active and return terminals 230 and 232 are coupled to the RF amplifier 228 through an isolation transformer 229. The RF amplifier 228 is configured to operate in a plurality of modes, during which the generator 200 outputs corresponding waveforms having specific duty cycles, peak voltages, crest factors, etc. In other embodiments, the generator 200 may be based on other types of suitable power supply topologies.

The controller 224 includes a processor 225 operably connected to a memory 226, which may include transitory type memory (e.g., RAM) and/or non-transitory type memory (e.g., flash media, disk media, etc.). The processor 225 includes an output port that is operably connected to the power supply 227 and/or RF amplifier 228 allowing the processor 225 to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then signals the power supply 227 and/or RF amplifier 228, which adjusts the DC and/or power supply, respectively. Those skilled in the art will appreciate that the processor 225 may be substituted for by using any logic processor (e.g., control circuit) adapted to perform the calculations and/or set of instructions described herein including, but not limited to, field programmable gate array, digital signal processor, and combinations thereof.

The generator 200 may include a plurality of sensors 280, e.g., an RF current sensor 280a, and an RF voltage sensor 280b. Various components of the generator 200, namely, the RF amplifier 228, the RF current and voltage sensors 280a and 280b, may be disposed on a printed circuit board (PCB). The RF current sensor 280a is coupled to the active terminal 230 and provides measurements of the RF current supplied by the RF amplifier 228. The RF voltage sensor 280b is coupled to the active and return terminals 230 and 232 and provides measurements of the RF voltage supplied by the RF amplifier 228. In embodiments, the RF current and voltage sensors 280a and 280b may be coupled to the active and return leads 228a and 228b, which interconnect the active and return terminals 230 and 232 to the RF amplifier 228, respectively.

The RF current and voltage sensors 280a and 280b provide the sensed RF voltage and current signals, respectively, to the controller 224, which then may adjust output of the power supply 227 and/or the RF amplifier 228 in response to the sensed RF voltage and current signals. The controller 224 also receives input signals from the input controls of the generator 200, the instrument 12 and/or forceps 22. The controller 224 utilizes the input signals to adjust power outputted by the generator 200 and/or performs other control functions thereon.

Figure 4:
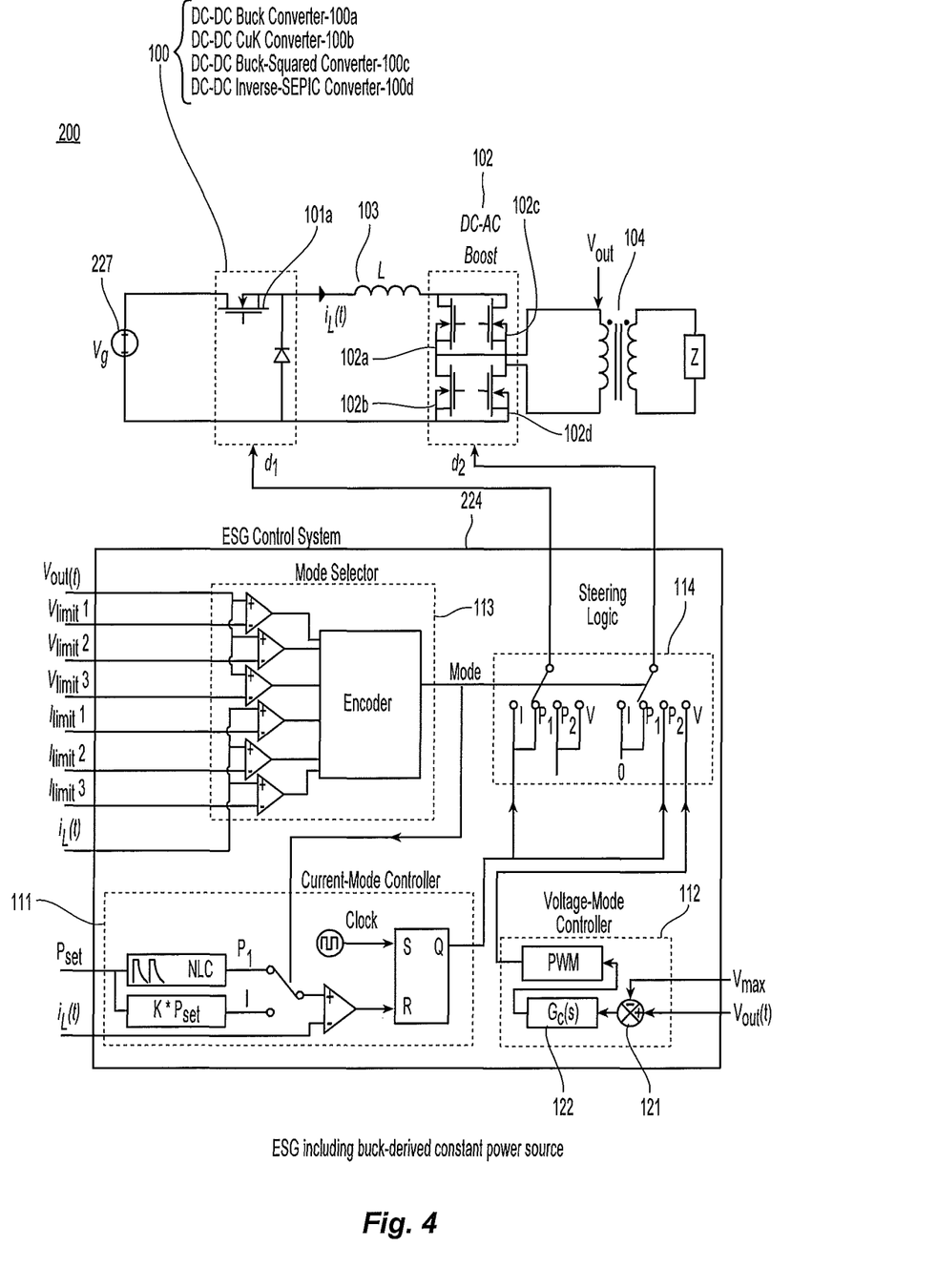
FIG. 4 is a schematic, block diagram of a DC-DC converter and a DC-AC inverter of the electrosurgical generator of FIG. 2 according to the present disclosure.

FIG. 4 shows another embodiment of the generator 200 configured to operate with near-deadbeat control to maintain a desired AC output of generator 200. As used herein, the terms "deadbeat" or "near-deadbeat" refer to adjustments being made by the generator 200 to the output from about 1 cycle of the waveform to about 100 cycles, and in certain embodiments from about 10 cycles to about 25 cycles. The term cycle refers to a full cycle of an electrosurgical alternating waveform having a positive and negative half cycle. The generator 200 according to the present disclosure may have an operating frequency of from about 100 kHz to about 1,000 kHz, and in certain embodiments, from about 200 kHz to about 500 kHz, thus the generator 200 operating at the predetermined frequency of 100 kHz outputs a waveform having 100,000 cycles per second. The adjustments to the output can be made at the same frequency (e.g., 1 cycle of the electrosurgical waveform) or a factor of about 0.1 (e.g., every 10 cycles of the electrosurgical waveform). In accordance with the instant disclosure, near-deadbeat control minimizes unintentional charring by ensuring that only a desired quantum of power is delivered to an electrosurgical instrument. In the prior art generators, slow transient response of the converter to changes in load impedance may result in excessive delivery of power that may not be detected for 500 cycles or more.

The generator 200 is also configured to operate in any of a constant voltage limit mode, a constant current limit mode, a constant power mode, and combinations thereof. The mode selection is generally based on the impedance associated with the tissue being cut. Different types of tissue, such as muscle and fat, have different impedances. In terms of electrosurgical operations, constant power output tends to uniformly vaporize tissue, resulting in clean dissection. Constant voltage output, on the other hand, tends to explosively vaporize or carbonize tissue ("black coagulation"), and constant current output tends to thermally coagulate tissue without vaporization ("white coagulation"). Carbonization is surgically useful if the surgeon wishes to rapidly destroy surface tissue, and thermal coagulation is regularly coupled with mechanical pressure to seal hepatic or lymphatic vessels shut. The surgeon, however, generally desires to operate using constant power output and importantly, return to using constant power output as quickly as possible if there is deviation.

Figure 5:
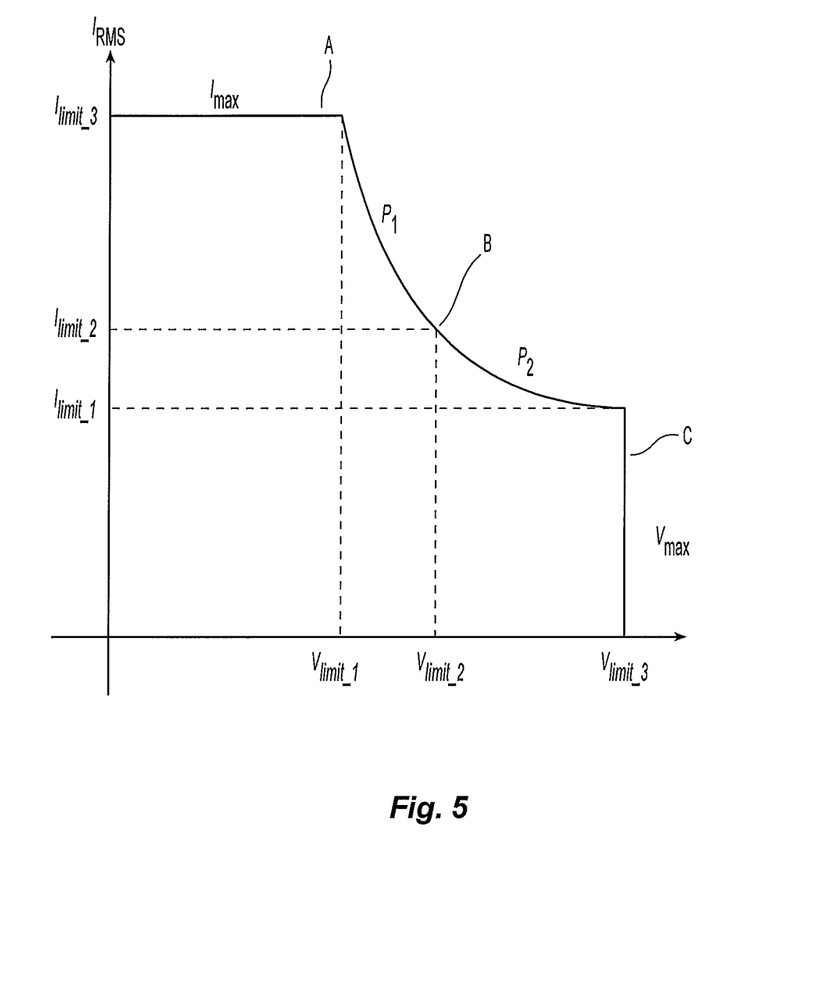
FIG. 5 is a graphical representation of desired output characteristics according to the present disclosure.

With respect to the AC output of the generator 200, and in embodiments, "constant power" is defined to mean the average power delivered in each switching cycle is substantially constant. Likewise, "constant voltage" and "constant current" are defined as modes where the root mean square (RMS) value of the AC voltage or current, respectively, is regulated to a substantially fixed value. A graphical representation of the desired output characteristics is illustrated in FIG. 5. As indicated in FIG. 5, as the load impedance increases and voltage increases, the corresponding increasing output voltage triggers a transition from a constant current mode shown as region A to a constant power mode shown as region B and to a constant voltage mode shown as region C. Similarly, as the load impedance decreases and current increases, the corresponding decreasing output voltage triggers the opposite transition from the constant voltage region C to the constant power region B and to the constant current region A.

With reference again to FIG. 4, the generator 200 includes one or more suitable converters 100. In embodiments, for example, the generator 200 may include a DC-DC buck converter 100a, DC-DC Ćuk converter 100b, DC-DC buck-squared converter 100c and DC-DC inverse-SEPIC converter 100d (or any other class of DC-DC converters containing an inductor in series with an output). Unless otherwise noted, for illustrative purposes, the generator 200 is described herein in terms of use with the DC-DC buck converter 100a.

In addition to the DC-DC buck converter, the generator 200 includes a DC-AC boost inverter 102, an inductor 103, a transformer 104, and the controller 224. In embodiments, the DC-DC buck converter 100a (or the other aforementioned converters) and the DC-AC boost inverter 102 are part of the RF output stage 228. In the illustrated embodiment, a DC voltage source Vg, such as the power supply 227, is connected to DC-DC buck converter 100a. Furthermore, inductor 103 is electrically coupled between DC-DC buck converter 100a and DC-AC boost inverter 102. The output of the DC-AC boost inverter 102 transmits power to the primary winding of transformer 104, which passes through the secondary winding of transformer 104 to the load Z (e.g., tissue being treated).

The DC-DC buck converter 100a includes a switching element 101a and the DC-AC boost inverter 102 includes a plurality of switching elements 102a-102d arranged in an H-bridge topology. In embodiments, the DC-AC boost inverter 102 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In the illustrated embodiment, controller 224 is in communication with both the DC-DC buck converter 100a and DC-AC boost inverter 102 via the switching elements 101a and 102a-102d, respectively. The controller 224 is configured to output control signals, which may be a pulse-width modulated signal, to the switching elements 101a and 102a-102d as described in further detail below with respect to the voltage-mode controller 112. In particular, the controller 224 is configured to control the duty cycle d1 of the control signal supplied to the switching element 101a of the DC-DC buck converter 100a and the duty cycle d2 of the control signals supplied to the switching elements 102a-102d of the DC-AC boost inverter 102. Additionally, controller 224 is configured to measure power characteristics of generator 200, and control generator 200 based at least in part on the measured power characteristics. Examples of the measured power characteristics include the current through inductor 103 and the voltage at the output of DC-AC boost inverter 102. In the illustrated embodiment, controller 224 controls the buck converter 100a by generating the duty cycle d1 based on a comparison of the inductor current and a nonlinear carrier control current for every cycle.

In accordance with the instant disclosure, controller 224 includes a current-mode controller 111, a voltage-mode controller 112, a mode selector 113, and steering logic 114. The mode selector 113 compares the output voltage $V_{out}(t)$ and the inductor current $i_L(t)$ to set limits in order to determine the desired mode of operation of the generator 200. The operational mode may be of constant (or maximum) current $I_{max}$ (e.g., constant current region A), constant power $P_1$ from DC-DC buck converter 100a, constant power $P_2$ from DC-AC boost inverter 102 (e.g., constant power region B), or constant (or maximum) voltage $V_{max}$ (e.g., constant voltage region C) as illustrated in FIG. 5, or combinations thereof. The output selection of mode selector 113 is communicated to steering logic 114. In the illustrated embodiment, steering logic 114 controls which of at least one of current-mode controller 111 and voltage mode controller 112 are enabled. Furthermore, steering logic 114 selects which conversion stage receives the output of current-mode controller 111 and/or voltage-mode controller 112.

In an embodiment, steering logic 114 switches between operating either the DC-DC buck converter 100a (and/or the other aforementioned converters) or DC-AC boost inverter 102 with current-mode control for constant power, depending on which portion of the desired output characteristics is being produced. The voltage mode controller 112 and/or current mode controller 111 adjust the duty cycles d1 and/or d2 for current mode control. Furthermore, steering logic 114 selects the duty cycle that each of DC-DC buck converter 100a and/or DC-AC boost inverter 102 receives.

The current-mode controller 111 compares the inductor current $i_L(t)$ to nonlinear carrier control current $i_C(t)$ (e.g., desired set point current). In the illustrated embodiment, the nonlinear carrier control current $i_C$ is set by the selection of Pset (e.g., desired power set point), which may be done by a user, or provided by a lookup table. In the illustrated embodiment, current-mode controller 111 uses a latch circuit to compare inductor current $i_L(t)$ to either a current limit signal (I) or a power limit signal ($P_1$). The control signal for the latch circuit is the mode signal, which is communicated from steering logic 114. The inputs of the latch circuit are a clock signal and either the current limit signal (I) or a power limit signal ($P_1$). The selection of the current-mode controller 111 output is in response to the current mode of the generator 200. The operating mode of the generator 200 may be communicated by the mode selector 113. The switching waveform d(t) is switched "high" at the start of a switching period if the inductor current $i_L(t)$ is lower than nonlinear carrier control current $i_C(t)$. Furthermore, the switching waveform d(t) is switched "low" in response to the inductor current $i_L(t)$ exceeding the nonlinear carrier control current $i_C(t)$. In other words, a comparison of the inductor current $i_L(t)$ to nonlinear carrier control current $i_C(t)$ facilitates adjusting pulse duration of duty cycle d1 of the buck converter 100a, as previously described.

To generate and control a constant current from generator 200, the average value of inductor current $i_L(t)$ is set to be substantially equal to fixed control current limit K*Pset. For small inductor current ripple, in other words $\Delta i_L \ll I_L$, the current-mode controller regulates the inductor current $i_L(t)$ to an approximately constant value, which is substantially equal to the fixed control current limit. In embodiments, the current-mode controller 111 is able to maintain an approximately constant value of inductor current $i_L(t)$ by adjusting the current within from about 1 cycle to about 100 cycles, in embodiments from about 2 to about 20 cycles, in further embodiments, from about 3 to about 10 cycles. This low cycle adjustment provides for near-deadbeat or deadbeat control as described above.

Continuing with reference to FIG. 4, voltage-mode controller 112 of the controller 224 includes a comparator 121, a compensator 122, and a pulse-width modulator (PWM) 123. Voltage-mode controller 112 compares the output voltage $V_{out}(t)$ with a reference voltage $V_{max}$ at comparator 121. The output of comparator 121 is communicated to compensator 122, which in turn, outputs an error signal that drives PWM 123. The output of compensator 122 is passed through PWM 123, which sets the duty cycle d2 of the signal in certain modes.

Furthermore, mode selector 113 includes an encoder and performs multiple comparisons. Specifically, and with respect to FIG. 5, the mode selector 113 uses the voltage comparison signals and the current comparison signals to determine whether generator 200 is operating in the constant current output region (A), the region P1 of the constant power output region (B), the region P2 of the constant power output region (B), or the constant voltage output region (C). Furthermore, the output mode signal from mode selector 113 controls the switch position in steering logic 114. When output voltage $V_{out}(t)$ exceeds the first voltage limit $V_{limit\_1}$, the second voltage limit $V_{limit\_2}$, and the third voltage limit $V_{limit\_3}$, then the encoder selects the constant voltage mode. The constant voltage mode signal from mode selector 113 causes the position of the switches of steering logic 114 to a "V" position as illustrated in FIG. 5 and Table 1 below, which shows duty cycle of DC-DC buck converter 100a and DC-AC boost inverter 102 by operating mode. As can be appreciated, the below operating modes may also be utilized with the other aforementioned converters.

TABLE 1

|  | $I_{max}$ | P1 | P2 | $V_{max}$ |
| --- | --- | --- | --- | --- |
| Buck Converter (or the other aforementioned converters) | Current-programmed mode (CPM) controlled with fixed control current limit | CPM controlled with nonlinear carrier control limit | 1 | 1 |
| Boost inverter | 1 | 1 | CPM controlled with fixed control current limit | Voltage mode controlled |

In various alternative embodiments, the selection of operating modes is based in part on the duty cycle. For example, if the generator 200 is operating in constant power mode using the DC-DC buck converter 100a and the duty cycle reaches 100% active (or any fixed duty cycle, e.g., less than 100%), the controller 224 may be configured to switch to the constant power region A using the DC-AC boost inverter 102. The switch to the boost inverter enables the generator 200 to operate over a higher range of impedances.

With respect to constant power output mode, constant AC power output is achieved by setting one or both of duty cycle d1 and duty cycle d2 to desired values. Moreover, generator 200 operates with constant AC power output in either a first constant power region P1 or a second constant power region P2. In various embodiments, the converter switches of the steering logic 114 between generating constant power using DC-DC buck converter 100a or DC-AC boost inverter 102, depending on the impedance of the load. Moreover, in various embodiments, generator 200 may operate both DC-DC buck converter 100a and/or DC-AC boost inverter 102 at the same time, which results in a constant power output having a high voltage and low power.

In steady-state and operating in first constant power region P1, inductor current $i_L(t)$ is compared to a nonlinear carrier control current $i_C(t)$ in current-mode controller 111. The pulse duration of the duty cycle d1 of the DC-DC buck converter 100a is varied using the current mode controller 111. The varying pulse duration of the duty cycle controls the inductor current $i_L(t)$, which is responsive to the load in contact with the DC-DC buck converter 100a. As the impedance of the load varies, the voltage across and the current through the inductor 103 also vary. As previously described, at the beginning of the duty cycle, the active portion of the duty cycle is initiated. In response to the inductor feedback signal exceeding the nonlinear carrier control current, the duty cycle switches to the non-active portion. The duty cycle stays in the non-active portion until the end of the duty cycle, upon which the next duty cycle begins in the active portion. In alternative embodiments, during the comparison of the inductor feedback signal and the nonlinear carrier control current, once the control current exceeds the inductor current, the duty cycle switches to the active portion. In accordance with the illustrated embodiment, generator 200 generates constant power using DC-DC buck converter 100a.

In steady-state and operating in second constant power region P2, the average voltage of $V_1(t)$ is constant in response to the input voltage Vg being constant, the DC-DC buck converter 100a is ran at a fixed duty cycle, since there is no average voltage across inductor 103. The use of current programmed mode control results in the average current of $i_L(t)$ being regulated to an approximately fixed value with deadbeat or near-deadbeat control. In order to regulate $i_L(t)$, duty cycle d2 is varied by the current mode controller to maintain $i_L(t)$ at a fixed value. Given the fixed voltage and current, the power at input of DC-AC boost inverter 102 is also constant. In accordance therewith, the DC-AC boost inverter 102 is nearly lossless, resulting in the output power being approximately equal to the input power. Since the input power is constant, the output power of DC-AC boost inverter 102 is also constant.

With respect to constant voltage output mode, constant voltage output is achieved by setting duty cycle d1 of DC-DC buck converter 100a to a fixed value, and duty cycle d2 of DC-AC boost inverter 102 is voltage-mode controlled. In the illustrated embodiment, the voltage-mode control involves measuring the output voltage of DC-AC boost inverter 102 with a sensor network, feeding the sensed output voltage to a control loop in voltage-mode controller 112, and adjusting the converter's duty cycle command based on the relative difference between the measured output voltage and the reference output voltage. In other words, the duty cycle d2 is set to increase or decrease the output voltage to match $V_{limit}$. $V_{limit}$ may be set by a user or based on values in a look-up table. Alternatively, the boost inverter may be run at a fixed duty cycle with no feedback of the output voltage.

With respect to constant current output mode, constant current output is achieved by operating DC-AC boost inverter 102 at a fixed duty cycle d2 and current-mode controlling DC-DC buck converter 100a. The current-mode control accurately controls the average inductor current such that the output of buck converter 100a is a constant current. In one constant current embodiment, current-mode controller 111 compares inductor current $i_L(t)$ to a constant current $i_c$, which is set by K*Pset, where K*Pset is a constant current set by the user during use. In various embodiments, Pset is set during the design stage.

In other words, controller 224 is configured to vary duty cycle d1 in order to maintain inductor current $i_L(t)$ at the fixed value. As a result, the constant current output mode produces an AC output current whose magnitude is regulated with near-deadbeat speed. In an exemplary embodiment, the generator 200 implementing the three modes of constant power, constant voltage, or constant current produces a very fast, very accurate regulation of the AC output characteristic. Various modes are impacted by monitored characteristics, while other modes do not need to respond to the same monitored characteristics. Specifically, controller 224 may switch between operating modes based in part on monitored characteristics, such as inductor current and voltage. In other words, the selection of which stage of the converter to current-mode control is achieved with minimal feedback and without a need for extraneous measurements, averaging, or feedback of the output. Also, and as previously mentioned, the controller 224 performs near deadbeat control by regulating inductor current to an approximately constant value, equal to a reference current.

Transitioning between the three modes, in an embodiment, is determined by monitoring the voltage of the primary winding of transformer 104 and the inductor current. Furthermore, the determination of transitioning between the modes is also based on the voltage and current of inductor 103. The controller 224 transitions modes from constant current to constant power to constant voltage as the output voltage increases. Specifically, in an embodiment, the generator 200 operates in the constant current mode if the output voltage is less than a first voltage limit ($V_{limit\_1}$). If the output voltage exceeds the first voltage limit, the generator 200 transitions to a first constant power mode (P1). If the output voltage exceeds a second voltage limit ($V_{limit\_2}$), the generator 200 transitions to a second constant power mode (P2). If the output voltage exceeds a third voltage limit ($V_{limit\_3}$), the generator 200 transitions to the constant voltage mode, where the output voltage is limited and held constant. In an embodiment, the first voltage limit ($V_{limit\_1}$), the second voltage limit ($V_{limit\_2}$), and the third voltage limit ($V_{limit\_3}$) are set by a user or by the generator 200 (e.g., from a look-up table).

Similarly, controller 224 transitions from constant voltage mode to constant power mode and to constant current mode as inductor current $i_L(t)$ increases. Specifically, in an embodiment, the generator 200 operates in the constant voltage mode if the inductor current does not exceed a first current limit ($I_{limit\_1}$). If the inductor current does exceed the first current limit ($I_{limit\_1}$), then the mode transitions to the second constant power mode (P2). If the inductor current exceeds a second current limit ($I_{limit\_2}$), then the mode transitions to the first constant power mode (P1). If the inductor current exceeds a third current limit ($I_{limit\_3}$), the generator 200 transitions to the constant current mode, where the inductor current is limited and held constant. In an embodiment, the first current limit ($I_{limit\_1}$), the second current limit ($I_{limit\_2}$), and the third current limit ($I_{limit\_3}$) are set by a user or by the generator (e.g., from a look-up table).

As described above, in order to achieve the constant current region A, the DC-DC buck converter 100a is controlled in current-program mode (CPM) and the DC-AC boost inverter 102 is fixed at about 100% duty cycle d2. In order to achieve the constant power region B, in one embodiment the DC-DC buck converter 100a is controlled in non-linear carrier control (NLC) mode and the DC-AC boost inverter 102 is fixed at about 100% duty cycle d2. In other embodiments, the DC-DC buck converter 100a may be fixed at about 100% duty cycle d1 and the DC-AC boost inverter 102 is controlled in CPM. In order to achieve the constant voltage region B, the DC-DC buck converter 100a is fixed at 100% duty cycle d1 and the DC-AC boost inverter 102 is fixed at a predetermined duty cycle d2, which may be less than 100%.

Switching between the constant current, power, and voltage regions A, B, and C may be based on a determination (e.g., experimentally or empirically) of duty cycles d1 and d2 for a particular current limit, power setting, and voltage limit and storing the values in a look-up table accessible by the controller 224. The control scheme of each region is changed by observing the duty cycle of the DC-DC buck converter 100a and/or DC-AC boost inverter 102 being controlled. Once the duty cycles d1 or d2 reach a predetermined threshold the controller 224 changes to the corresponding new scheme. This control scheme relies on the controller 224 having preprogrammed duty cycle values for a given current, power, or voltage set point stored in a look-up table. This, however, requires a complicated (e.g., three-dimensional table) table that needs to be experimentally derived for each individual generator 200. As can be appreciated, this may not be labor and cost-effective and may be prone to error due to component tolerances of the generator 200 as well as human error. Moreover, the inductor 103 may need to have a sufficiently large inductance in order to achieve exact control of power when operating the DC-AC boost inverter 102 in CPM.

Accordingly, the present disclosure provides a system and method for determining duty cycles d1 and d2 with reduced complexity and increases power control accuracy while reducing required inductor size of the inductor 103 and also allows for independent and dynamic control of a crest factor (CF) and power of the delivered electrosurgical waveform. In particular, the DC-AC boost inverter 102 may be used to control the CF of the waveform while the DC-DC buck converter 100a is used to control the output power. In this embodiment, DC-AC boost inverter 102 is fixed at a given cycle, which may be from about 0% to about 100%, in embodiments, from about 20% to about 90%, while the DC-DC buck converter 100a is run in NLC control.

Moreover, the present disclosure provides for a system and method of switching between constant current, power, and voltage regions A, B, and C based on the duty cycle d1 of DC-DC buck converter 100a as determined by the mode selector 113, while keeping the duty cycle d2 of the DC-AC boost inverter 102 fixed, rather than using the voltage limits ($V_{limit\_1}$, $V_{limit\_2}$, $V_{limit\_3}$) and current limits ($I_{limit\_1}$, $I_{limit\_2}$, $I_{limit\_3}$). Specifically, in order to determine whether the DC-DC buck converter 100a can control power while the duty cycle d2 of the DC-AC boost inverter 102 is fixed, the average switch model of each of the DC-DC buck converter 100a and the DC-AC boost inverter 102 may be used in a steady-state to determine a duty cycle d1 of DC-DC buck converter 100a as a function of the load. The duty cycle d1 for operating the DC-DC buck converter 100a in CPM while the duty cycle d2 of the DC-AC boost inverter 102 is automatically controlled by the controller 224 by comparing the measured inductor current with the current limits ($I_{limit\_1}$, $I_{limit\_2}$, $I_{limit\_3}$).

Figure 6:
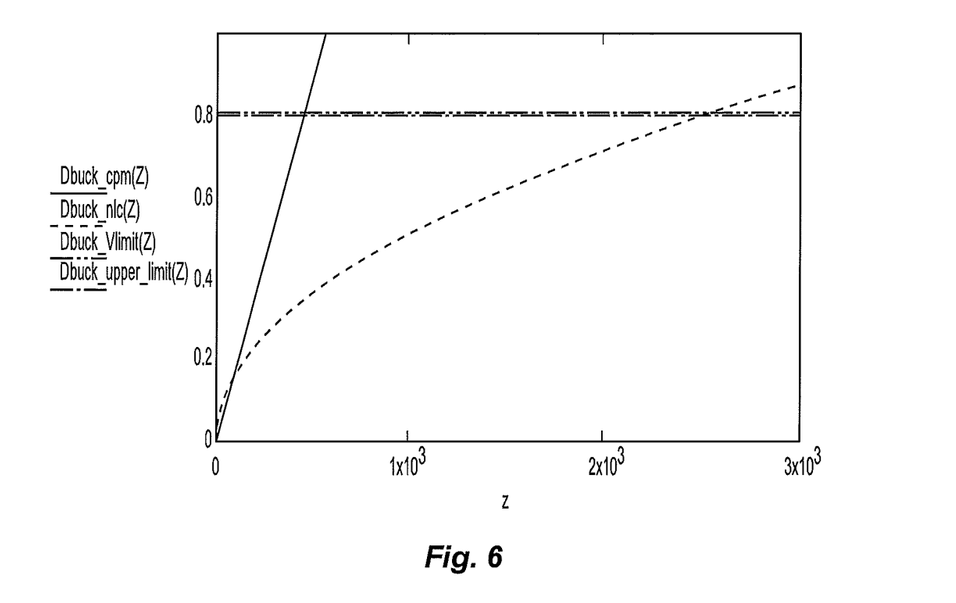
FIG. 6 is a graphical representation of duty cycles of a DC-DC buck converter of the generator of FIG. 2 as a function of impedance according to the present disclosure.
Figure 7:
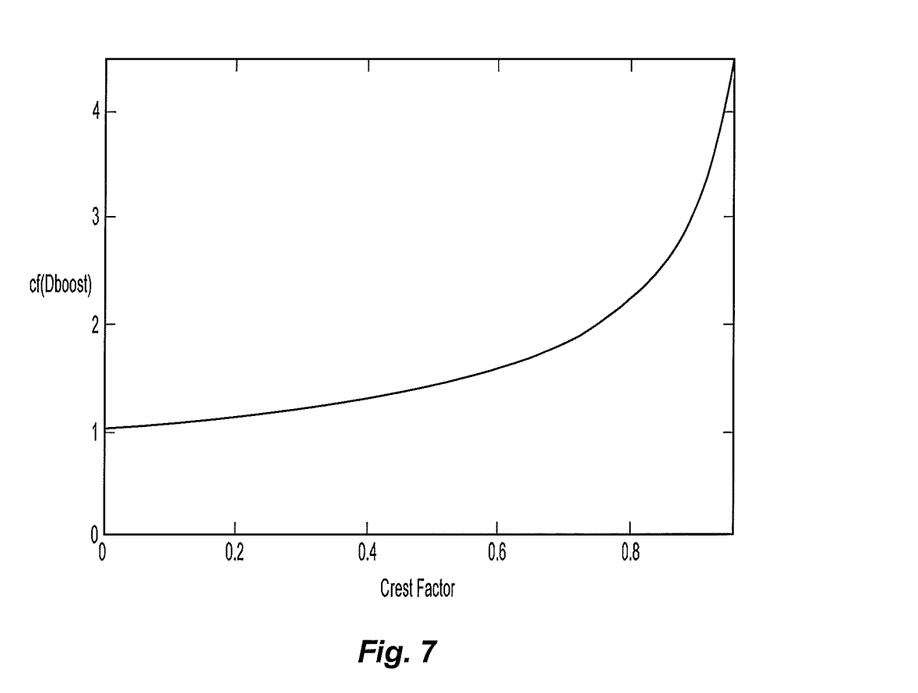
FIG. 7 is a graphical representation of a crest factor as a function of the duty cycle of the DC-DC buck converter according to the present disclosure.

FIG. 6 shows plots of duty cycles of DC-DC buck converter 100a as a function of impedance for impedance limits for duty cycle d1 while in CPM, NLC, and voltage limit modes. The portion within the plots illustrates the dynamic range of the DC-DC buck converter 100a. The plot of FIG. 6 also illustrates that the duty cycle of the DC-DC buck converter 100a may be saturated once the current or voltage limits are reached rather than having the controller 224 calculate the duty cycle d1 of the DC-DC buck converter 100a. Further, this allows for the DC-DC buck converter 100a to control power while the DC-AC boost inverter 102 is fixed, such that the duty cycle d2 controls the crest factor independently of the duty cycle d1 as illustrated in FIG. 7, which shows a plot of the crest factor as a function of the duty cycle d1.

By setting the duty cycle d2 to a fixed value to achieve a desired crest factor, the controller 224 can independently set the crest factor as well as Vrms as long as the duty cycle d1 does not saturate. The duty cycles d1 and d2 may be changed dynamically by the controller 224 to achieve different tissue effects. Changing the crest factor of the waveform allows for changing between different RF modes such as cutting and coagulation or a variety of blend modes.

Further, the present disclosure also provides for an improved NLC waveform for controlling the DC-DC buck converter 100a. While the DC-DC buck converter 100a is operated in NLC control with a fixed DC-AC boost inverter 102, the power droops with increasing load resistance. This corresponds to lower DC current in the inductor 103. The present disclosure provides for increasing the DC current at load resistances, thereby modifying the NLC waveform to account for inaccuracies, losses and/or other non-idealities.

Figure 8:
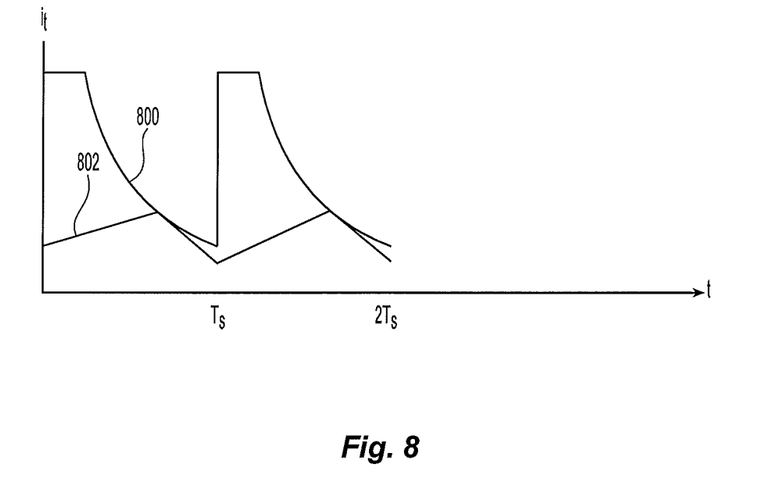
FIG. 8 is a graphical representation of a non-modified waveform output by the DC-DC buck converter according to the present disclosure.

For the DC-DC buck converter 100a, a non-modified NLC waveform follows formula (I) below:

$$i_c = \frac{P_{set} T_s}{t V_g} \qquad (I)$$

In formula (I), Pset is the power set point, Ts is the switching period of the switching element 101, Vg is the input DC voltage supplied by the power supply 227, and t is time. The resulting non-modified waveform 800 of the DC-DC buck converter 100a is shown in FIG. 8, which saturates for a small t and follows the formula (I) for the rest of the switching period. FIG. 8 also shows the current waveform $i_L(t)$ 802 of the inductor 103.

In embodiments where the generator 200 utilizes the DC-DC Ćuk converter 100b or the DC-DC inverse-SEPIC 100d, a non-modified NLC waveform follows formula (II) below:

$$i_c = \frac{P_{set} \cdot (t - T_s)}{t \cdot V_g} \qquad (II)$$

In an embodiment where the generator 200 utilizes DC-DC buck-squared 100c, a non-modified NLC waveform follows formula (III) below:

$$i_c = \frac{P_{set} \cdot T_s^2}{t^2 \cdot V_g} \qquad (III)$$

Figure 9:
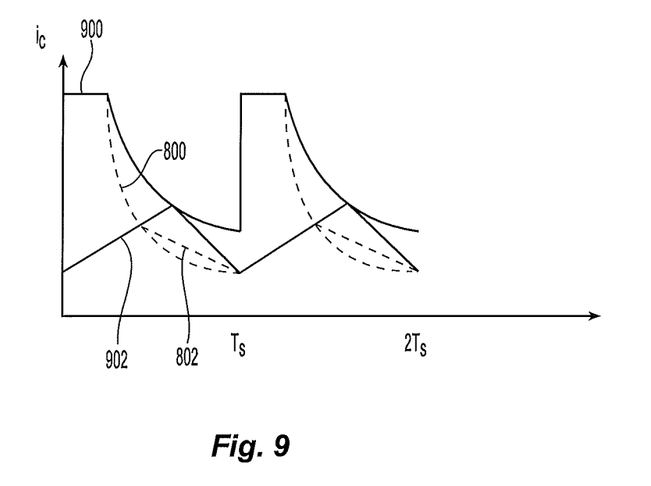
FIG. 9 is a graphical representation of a modified waveform output by the DC-DC buck converter according to the present disclosure.

For illustrative purposes, a modified NLC waveform 900 as provided by the DC-DC buck converter 100a is shown in FIG. 9 and includes a power set point that includes a time variable, namely a ratio of the time period. In particular, Pset may be defined using the formula (IV) below:

$$P_{set} = P + P_{comp} \frac{t}{T_s} \qquad (IV)$$

In formula (IV), P is the nominal set point and Pcomp is the gain of the linear portion of the formula (IV) used to compensate for non-idealities. Formula (V) includes the time-variable Pcomp and is listed below:

$$i_c = \frac{[P + P_{comp}(t)]T_s}{tV_g} \qquad (V)$$

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator, comprising:
   at least one DC-DC Ćuk converter configured to output a DC waveform and a nonlinear carrier control current that is based on a time-variable power set point;
   at least one boost inverter coupled to the at least one converter, the at least one boost inverter configured to convert the DC waveform to generate at least one electrosurgical waveform;
   at least one inductor connected in series with the at least one DC-DC Ćuk converter and the at least one boost inverter, the at least one inductor configured to output an inductor current; and at least one controller coupled to the at least one DC-DC Ćuk converter and the at least one boost inverter and configured to maintain the inductor current at a predetermined value by controlling a pulse duration of a duty cycle of the at least one DC-DC Ćuk converter based on a comparison of the inductor current and the nonlinear carrier control current, the at least one controller further configured to control a crest factor (CF) of the at least one electrosurgical waveform using the at least one boost inverter, wherein the at least one DC-DC Ćuk converter and the at least one boost inverter include a plurality of switching elements arranged in an H-bridge topology, wherein the time-variable set point is determined as $$P_{set} = P + P_{comp}\frac{t}{T_s},$$

and wherein P is a nominal power set point, $P_{comp}$ is a factor configured to compensate for non-idealities, t is time, and $T_s$ is a switching period of at least one of the switching elements.

2. The electrosurgical generator according to claim 1, wherein the at least one controller is configured to adjust the duty cycle of the at least one DC-DC Ćuk converter and a duty cycle of the at least one boost inverter to operate the at least one electrosurgical waveform in at least one of constant current, constant voltage, or constant power modes.

3. The electrosurgical generator according to claim 2, wherein the at least one DC-DC Ćuk converter includes at least one first switching element operated at the duty cycle of the at least one DC-DC Ćuk converter and the at least one boost inverter includes at least one second switching element operated at the second duty cycle of the at least one boost inverter.

4. The electrosurgical generator according to claim 2, wherein the at least one controller is configured to control the at least one DC-DC Ćuk converter in a current-program mode and to maintain the duty cycle of the at least one boost inverter at about 100% to operate the at least one electrosurgical waveform in a constant current mode.

5. The electrosurgical generator according to claim 2, wherein the at least one controller is configured to control the at least one DC-DC Ćuk converter in a non-linear carrier control mode and to maintain the duty cycle of the at least one boost inverter at about 100% to operate the at least one electrosurgical waveform in a constant power mode.

6. The electrosurgical generator according to claim 2, wherein the at least one controller is configured to control the at least one boost inverter in a current-program mode and to maintain the duty cycle of the at least one DC-DC Ćuk converter at about 100% to operate the at least one electrosurgical waveform in a constant power mode.

7. The electrosurgical generator according to claim 2, wherein the at least one controller is configured to maintain the duty cycle of the at least one DC-DC Ćuk converter at about 100% and the duty cycle of the at least one boost inverter at less than 100% to operate the at least one electrosurgical waveform in a constant voltage mode.

8. The electrosurgical generator according to claim 1, wherein the at least one controller is configured to switch operation of the at least one electrosurgical waveform between at least one of constant current, constant voltage, or constant power modes based on the duty cycle of the at least one DC-DC Ćuk converter or by monitoring a voltage of primary windings of a transformer of the electrosurgical generator and the inductor current.

9. An electrosurgical generator, comprising:

at least one DC-DC buck-squared converter configured to output a DC waveform and a nonlinear carrier control current that is based on a time-variable power set point;

at least one boost inverter coupled to the at least one converter, the at least one boost inverter configured to convert the DC waveform to generate at least one electrosurgical waveform;

at least one inductor connected in series with the at least one DC-DC buck squared converter and the at least one boost inverter, the at least one inductor configured to output an inductor current; and at least one controller coupled to the at least one DC-DC buck-squared converter and the at least one boost inverter and configured to maintain the inductor current at a predetermined value by controlling a pulse duration of a duty cycle of the at least one DC-DC buck-squared converter based on a comparison of the inductor current and the nonlinear carrier control current, the at least one controller further configured to control a crest factor (CF) of the at least one electrosurgical waveform using the at least one boost inverter, wherein the at least one DC-DC buck-squared converter and at least one boost inverter include a plurality of switching elements arranged in an H-bridge topology, wherein the time-variable set point is determined as $$P_{set} = P + P_{comp}\frac{t}{T_s},$$

and wherein P is a nominal power set point, $P_{comp}$ is a factor configured to compensate for non-idealities, t is time, and $T_s$ is a switching period of at least one of the switching elements.

10. The electrosurgical generator according to claim 9, wherein the at least one controller is configured to adjust the duty cycle of the at least one DC-DC buck-squared converter and a duty cycle of the at least one boost inverter to operate the at least one electrosurgical waveform in at least one of constant current, constant voltage, or constant power modes.

11. The electrosurgical generator according to claim 10, wherein the at least one DC-DC buck-squared converter includes at least one first switching element operated at the duty cycle of the at least one DC-DC buck-squared converter and the at least one boost inverter includes at least one second switching element operated at the second duty cycle of the at least one boost inverter.

12. The electrosurgical generator according to claim 10, wherein the at least one controller is configured to control the at least one DC-DC buck-squared converter in a current-program mode and to maintain the duty cycle of the at least one boost inverter at about 100% to operate the at least one electrosurgical waveform in a constant current mode.

13. The electrosurgical generator according to claim 10, wherein the at least one controller is configured to control the at least one DC-DC buck-squared converter in a non-linear carrier control mode and to maintain the duty cycle of the at least one boost inverter at about 100% to operate the at least one electrosurgical waveform in a constant power mode.

14. The electrosurgical generator according to claim 10, wherein the at least one controller is configured to control the at least one boost inverter in a current-program mode and to maintain the duty cycle of the at least one DC-DC buck-squared converter at about 100% to operate the at least one electrosurgical waveform in a constant power mode.

15. The electrosurgical generator according to claim 9, wherein the at least one controller is configured to switch operation of the at least one electrosurgical waveform between at least one of constant current, constant voltage, or constant power modes based on the duty cycle of the at least one DC-DC buck-squared converter or by monitoring a voltage of primary windings of a transformer of the electrosurgical generator and the inductor current.

16. An electrosurgical generator, comprising:
- at least one DC-DC inverse SEPIC converter configured to output a DC waveform and a nonlinear carrier control current that is based on a time variable power set point;
- at least one boost inverter coupled to the at least one converter, the at least one boost inverter configured to convert the DC waveform to generate at least one electrosurgical waveform;
- at least one inductor connected in series with the at least one DC-DC inverse SEPIC converter and the at least one boost inverter, the at least one inductor configured to output an inductor current; and
- at least one controller coupled to the at least one DC-DC inverse SEPIC converter and the at least one boost inverter and configured to maintain the inductor current at a predetermined value by controlling a pulse duration of a duty cycle of the at least one DC-DC inverse SEPIC converter based on a comparison of the inductor current and the nonlinear carrier control current, the at least one controller further configured to control a crest factor (CF) of the at least one electrosurgical waveform using the at least one boost inverter, wherein the at least one DC-DC inverse SEPIC converter and at least one boost inverter include a plurality of switching elements arranged in an H-bridge topology, wherein the time-variable set point is determined as $$P_{set} = P + P_{comp}\frac{t}{T_s},$$

and wherein P is a nominal power set point, $P_{comp}$ is a factor configured to compensate for non-idealities, t is time, and $T_s$ is a switching period of at least one of the switching elements.

* * * * *